(12) United States Patent
Whitten et al.

(10) Patent No.: US 7,652,134 B2
(45) Date of Patent: Jan. 26, 2010

(54) METHODS FOR CONVERTING QUINOLONE ESTERS INTO QUINOLONE AMIDES

(75) Inventors: Jeffrey P. Whitten, Santee, CA (US); Fabrice Pierre, La Jolla, CA (US); Collin Regan, San Diego, CA (US); Michael Schwaebe, San Diego, CA (US); George Petros Yiannikouros, Florence, SC (US); Michael Jung, Los Angeles, CA (US)

(73) Assignee: Cylene Pharmaceuticals, Inc., San Diego, CA (US)

( * ) Notice: Subject to any disclaimer, the term of this patent is extended or adjusted under 35 U.S.C. 154(b) by 498 days.

(21) Appl. No.: 11/149,007

(22) Filed: Jun. 9, 2005

(65) Prior Publication Data

US 2006/0063761 A1 Mar. 23, 2006

Related U.S. Application Data

(60) Provisional application No. 60/611,030, filed on Sep. 17, 2004.

(51) Int. Cl.
*C07D 413/14* (2006.01)
*C07D 401/14* (2006.01)
(52) U.S. Cl. .......................... 544/99; 544/329; 544/59
(58) Field of Classification Search .................. 544/99, 544/361, 59, 342; 546/66, 75
See application file for complete search history.

(56) References Cited

U.S. PATENT DOCUMENTS

| | | | |
|---|---|---|---|
| 4,528,285 A | 7/1985 | Chu et al. | |
| 5,646,163 A | 7/1997 | Demuth et al. | |
| 6,645,981 B2 | 11/2003 | Ledoussal et al. | |
| 6,821,969 B2 * | 11/2004 | Thorarensen | 514/230.2 |
| 6,900,224 B2 | 5/2005 | Ledoussal et al. | |
| 7,141,565 B1 * | 11/2006 | Whitten et al. | 514/229.5 |
| 2002/0025960 A1 | 2/2002 | Bundy et al. | |
| 2004/0029882 A1 | 2/2004 | Ledoussal et al. | |
| 2005/0203120 A1 | 9/2005 | Adelman et al. | |
| 2005/0215583 A1 | 9/2005 | Arkin et al. | |

FOREIGN PATENT DOCUMENTS

| | | |
|---|---|---|
| EP | 0 058 392 | 8/1982 |
| WO | WO-89/12055 | 12/1989 |
| WO | WO-92/03136 | 3/1992 |
| WO | WO-95/29894 | 11/1995 |
| WO | WO-02/17916 | 3/2002 |
| WO | WO-2004/014893 | 2/2004 |
| WO | WO-2004/091504 | 10/2004 |
| WO | WO-2005/089756 | 9/2005 |
| WO | WO-2005/089757 | 9/2005 |

OTHER PUBLICATIONS

Han et al., Trends Pharm. Sci. (2000) 21:136-142.
Satchell and Satchell, Chem. Rev. (1969) 69:251-278.
Database CA [Online], database accession No. 1997:692822.
Database CA [Online], database accession No. 1997:522331.
Database CA [Online], database accession No. 1997:70540.
Database CA [Online], database accession No. 1989:632785.
Database CA [Online], database accession No. 1987:18529.
Database CA [Online], database accession No. 1983:575560.
Database Chemcats, accession No. 2003:2367544.
International Search Report for PCT/US2005/033323, mailed on Jul. 4, 2006, 11 pages.
Kim et al., Bioorganic & Medicinal Chemistry Letters (1995) 5(17):1953-1956.
Kim, Journal of Heterocyclic Chemistry (1981) 18(7):1389-1392.
Schroeder et al., Journal of Heterocyclic Chemistry (1988) 25(6):1769-1772.
Wang et al., Tetrahedron Letters (2001) 42(13):2553-2555.
U.S. Appl. No. 06/604,208, filed by Daniel Tim-Wo Chu in Apr. 1984.
Cecchetti et al., Bioorganic & Medicinal Chemistry (1997) 5(7):1339-1344.
Chu et al., J. Med. Chem. (1986) 29:1531-1534.
Chung and Kim, Tetrahedron (1995) 51(46):12549-12562.
Kondo et al., J. Med. Chem. (1990) 33:2012-2015.
Wentland et al., J. Med. Chem. (1993) 36:1580-1596.
Barn et al., Tetrahedron Letters (1996) 37(18):3213-3216.
European Search Report for EP 05813754.8, mailed Aug. 13, 2008, 6 pages.
Dorwald, Side Reactions in Organic Synthesis, Wiley: VCH, Weinheim, 2005, p. IX of Preface.
Non-Final Office Action for U.S. Appl. No. 11/228,636, mailed on Sep. 30, 2008, 12 pages.

* cited by examiner

Primary Examiner—Charanjit S Aulakh
(74) Attorney, Agent, or Firm—Morrison & Foerster LLP

(57) ABSTRACT

The present invention relates to methods of preparing compounds having formula (1), (2), (5), and ((6A)-(6D))

(1)

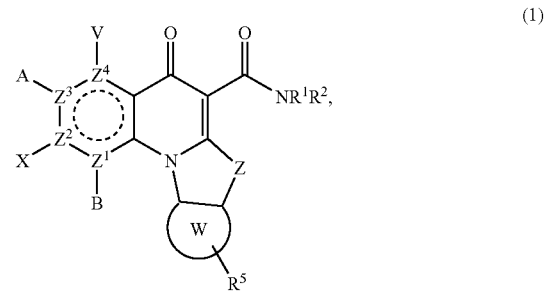

-continued (2)
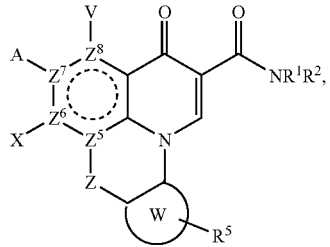

(5)
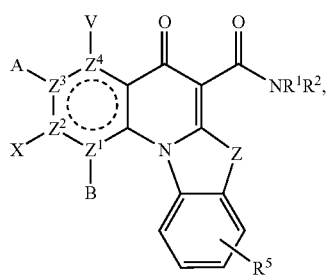

(6A)
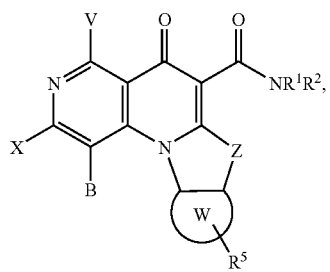

(6B)
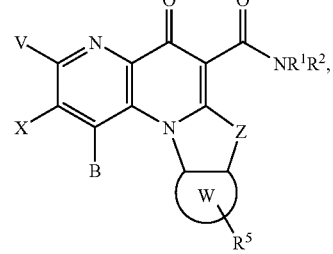

(6C)
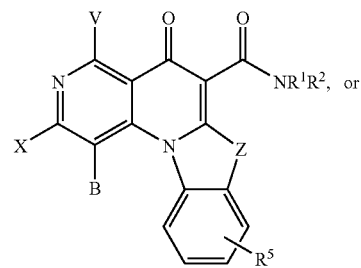

(6D)
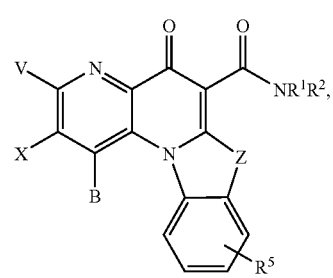

comprising contacting the corresponding ester, an amine with formula $NHR^1R^2$, and a Lewis acid having formula $ML_n$, wherein L is a halogen atom or an organic radical, n is 3-5, and M is a group III elemental atom, a group IV elemental atom, As, Sb, V or Fe, wherein A, B, V, X, Z, W, $R^1$, $R^2$, $R^5$, $Z^1$, $Z^2$, $Z^3$, $Z^4$, $Z^5$, $Z^6$, $Z^7$, and $Z^8$ are substituents.

$Z^4$, $Z^5$, $Z^6$, $Z^7$, and $Z^8$ are substituents.

29 Claims, No Drawings

METHODS FOR CONVERTING QUINOLONE ESTERS INTO QUINOLONE AMIDES

CROSS REFERENCE

This application claims the benefit of priority of U.S. provisional patent application Ser. No. 60/611,030, filed Sep. 17, 2004, which is incorporated herein by reference.

BACKGROUND

Evidence suggests that quadruplex structures can exist in vivo in specific regions of the genome, including the telomeric ends of chromosomes and oncogene regulatory regions (Han, et al., *Trends Pharm. Sci.* (2000) 21:136-142). Quadruplex structures can form in certain purine-rich strands of nucleic acids. In duplex nucleic acids, certain purine rich strands are capable of engaging in a slow equilibrium between a typical duplex helix structure and in unwound and non-B-form regions. These unwound and non-B forms can be referred to as "paranemic structures." Some forms are associated with sensitivity to S1 nuclease digestion, which can be referred to as "nuclease hypersensitivity elements" or "NHEs." A quadruplex is one type of paranemic structure and certain NHEs can adopt a quadruplex structure.

SUMMARY OF THE INVENTION

The present invention provides methods for preparing compounds having formula 1

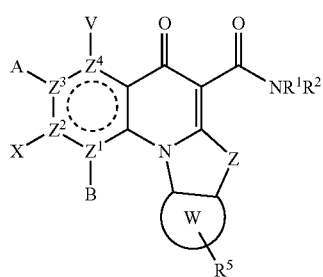

(1)

or formula 2

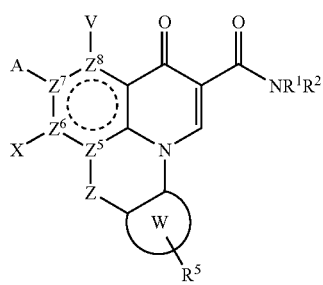

(2)

comprising contacting an ester, $NHR^1R^2$, and a Lewis acid, wherein said ester has formula 3

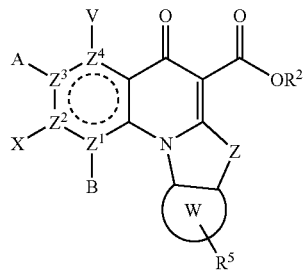

(3)

or formula 4

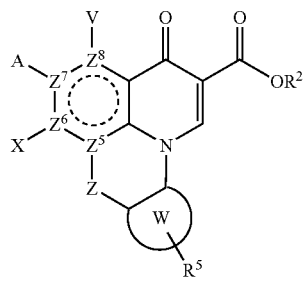

(4)

A, V, and X are independently H, halo, azido, $R^2$, $CH_2R^2$, $SR^2$, $OR^2$ or $NR^1R^2$; or wherein A and X, or A and V may form a carbocyclic ring, heterocyclic ring, aryl or heteroaryl, each of which may be optionally substituted and/or fused with a cyclic ring;

wherein $NR^1R^2$, $R^1$ and $R^2$ together with N may form an optionally substituted ring;

each Z is $CH_2$, O, S, or $NR^1$;

$Z^1$, $Z^2$, $Z^3$, $Z^4$, $Z^6$, $Z^7$, and $Z^8$ are independently C or N, provided any two N are non-adjacent;

$Z^5$ is C or N, provided $Z^5$ is C if Z is O, S or $NR^1$, and further provided that Z and $Z^6$ are not N if $Z^5$ is N;

each $R^1$ is H or a $C_{1-6}$ alkyl;

each $R^2$ is H or a $C_{1-10}$ alkyl or $C_{2-10}$ alkenyl optionally containing one or more non-adjacent heteroatoms selected from N, O, and S, and optionally substituted with a carbocyclic or heterocyclic ring; or $R^2$ is an optionally substituted carbocyclic ring, heterocyclic ring, aryl or heteroaryl;

each B is H or halo;

each W is an optionally substituted aryl or heteroaryl, which may be monocyclic, or fused with a single or multiple ring and optionally containing a heteroatom;

and each $R^5$ is a substituent at any position on the fused ring; and is H, $OR^2$, $NR^1R^2$, $C_{1-6}$ alkyl, $C_{2-6}$ alkenyl, each optionally substituted by halo, C=O or one or more heteroatoms; or $R^5$ is an inorganic substituent; or two adjacent $R^5$ is linked to obtain a 5-6 membered substituted or unsubstituted carbocyclic or heterocyclic ring, optionally fused to an additional substituted or unsubstituted carbocyclic or heterocyclic ring.

Furthermore, the present invention also provides methods for preparing compounds having the formula:

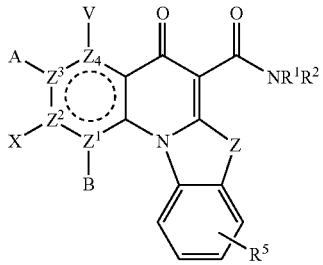
(5)

comprising contacting the corresponding ester with NHR$^1$R$^2$ and a Lewis acid, wherein each substituent is as defined in formula 1.

The present invention also provides methods for preparing compounds having formula 6A-6D

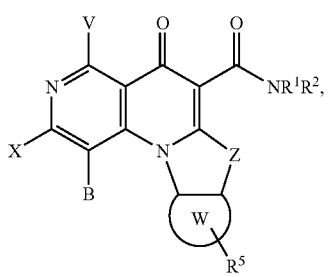
(6A)

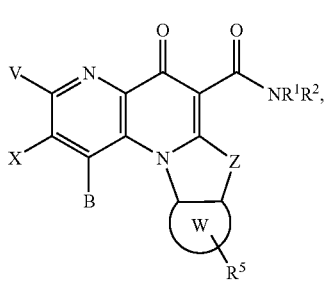
(6B)

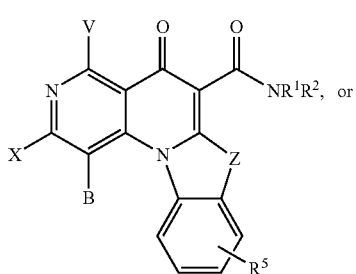
(6C)

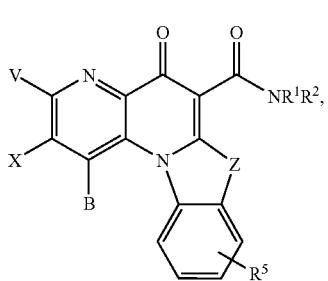
(6D)

comprising contacting the corresponding esters with NHR$^1$R$^2$ and a Lewis acid, wherein B, V, X, Z, R$^1$, R$^2$, W, and R$^5$ are as defined in formula 1.

The present methods involve amide coupling of an ester with an amine in the presence of a Lewis acid such as aluminum chloride. Suitable Lewis acids may be selected by conducting a test reaction, and observing the amount of reaction product produced, as described hereafter. The present methods do not require hydrolysis of the ester to a carboxylic acid prior to amide coupling. Thus, the present methods are simpler. As shown in Example 9, the present methods also provide higher yields and purity than previous methods involving requiring hydrolysis of the ester to the acid (Example 10).

In one embodiment, the Lewis acid has formula ML$_n$, wherein L is a halogen atom or an organic radical, n is 3-5, and M is a group III elemental atom, a group IV elemental atom, As, Sb, V or Fe.

In the above methods, the contacting step may be performed at room temperature. Alternatively, the ester, amine and Lewis acid may be contacted at cooler or elevated temperatures than room temperature, which may be determined by one skilled in the art.

In one example, the contacting step comprises contacting the ester and amine in an organic solvent to form a solution, and contacting the solution with a Lewis acid. In one example, the organic solvent is methylene chloride. The reaction may also be conducted using other suitable solvents known in the art.

In one embodiment, an excess of amine in relation to the ester may be used. For example, the ratio of the ester to the amine may be 1:2; 1:1.5; or 1:1.25.

In another embodiment, an equimolar amount of Lewis acid to the amine may be used. Alternatively, the amount of Lewis acid used may be more or less than the amine.

The above methods may further comprise isolating a compound having any one of the above formula. The isolated compounds may further be purified using any methods known in the art. For example, the isolated compounds may be purified through column chromatography, recrystallization, or both.

In the above methods, the purity of the isolated compounds may be between 90 and 99%. For example, the isolated compounds may have a purity between 90 and 95%.

In the above methods, the ester may be contacted with NHR$^1$R$^2$, wherein R$^1$ is a (CR$^3{}_2$)$_n$ group;

R$^2$ is NR$^3$R$^4$;

R$^3$ is H or C$_{1-6}$ alkyl;

n is 1-6; and

R$^4$ is H or a C$_{1-10}$ alkyl or C$_{2-10}$ alkenyl optionally containing one or more non-adjacent heteroatoms selected from N, O and S, and optionally substituted with a carbocyclic or heterocyclic ring; and wherein in NR$^3$R$^4$, R$^3$ and R$^4$ may form an optionally substituted ring such as those previously described above.

In the above methods, W if present in any of the above compounds may be selected from the group consisting of

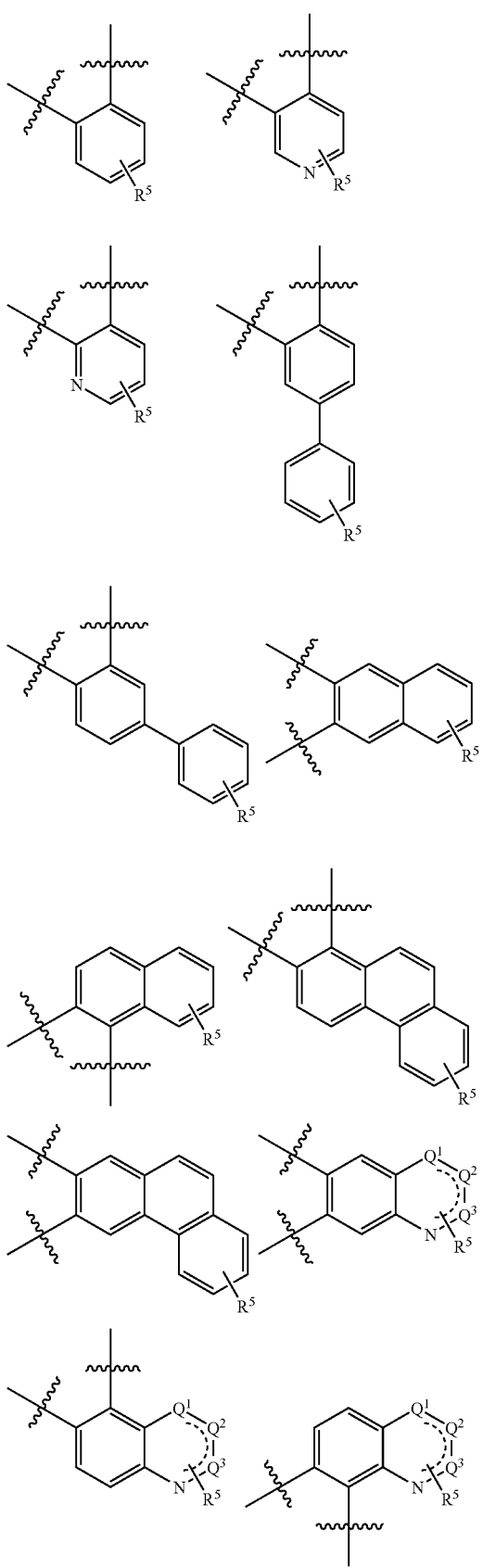
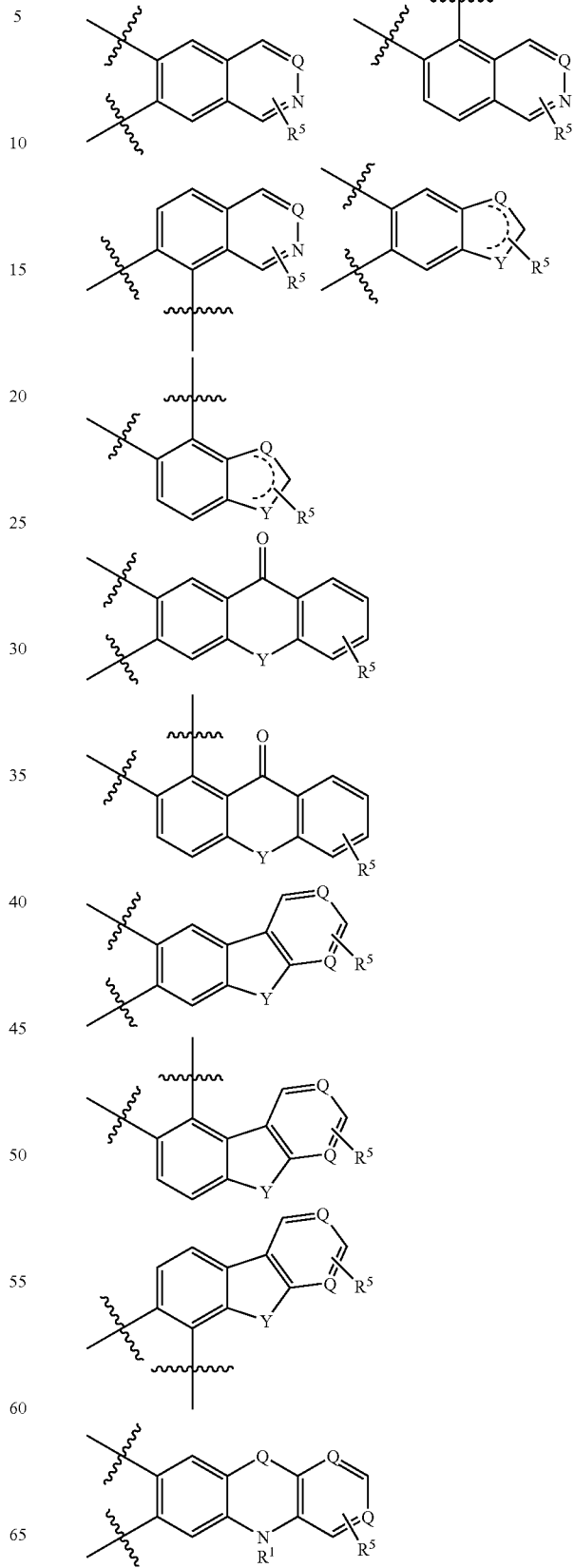

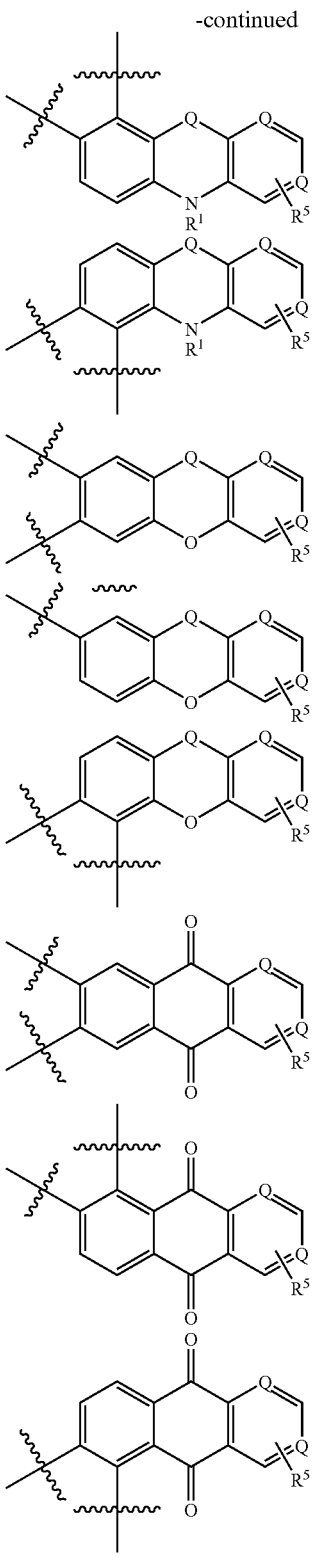

wherein each Q, $Q^1$, $Q^2$, and $Q^3$ is independently CH or N;
Y is independently O, CH, C=O or $NR^1$;
and $R^5$ is as defined above.

In the above methods, X in any of the above compounds may be $SR^2$, where $R^2$ is a $C_{0-10}$ alkyl or $C_{2-10}$ alkenyl optionally substituted with a heteroatom, a carbocyclic ring, a heterocyclic ring, an aryl or a heteroaryl. In one example, $R^2$ is a $C_{1-10}$ alkyl substituted with an optionally substituted pyrazine.

In the above methods, X and A in any of the above compounds may independently be halo or $NR^1R^2$, wherein $R^1$ may be H and $R^2$ may be a $C_{1-10}$ alkyl optionally substituted with a heteroatom, a $C_{3-6}$ cycloalkyl, aryl or a 5-14 membered heterocyclic ring containing one or more N, O or S. In one example, $R^2$ is a $C_{1-10}$ alkyl substituted with an optionally substituted heterocyclic ring, particularly a 5-14 membered heterocyclic ring. Alternatively, $R^1$ and $R^2$ together with N may form an optionally substituted heterocyclic ring containing one or more N, O or S, and particularly a 5-14 membered heterocyclic ring.

Examples of optionally substituted heterocyclic rings include but are not limited to tetrahydrofuran, 1,3-dioxolane, 2,3-dihydrofuran, tetrahydropyran, benzofuran, isobenzofuran, 1,3-dihydro-isobenzofuran, isoxazole, 4,5-dihydroisoxazole, piperidine, pyrrolidine, pyrrolidin-2-one, pyrrole, pyridine, pyrimidine, octahydro-pyrrolo[3,4-b]pyridine, piperazine, pyrazine, morpholine, thiomorpholine, imidazole, aminodithiadiazole, imidazolidine-2,4-dione, benzimidazole, 1,3-dihydrobenzimidazol-2-one, indole, thiazole, benzothiazole, thiadiazole, thiophene, tetrahydro-thiophene 1,1-dioxide, diazepine, triazole, guanidine, diazabicyclo[2.2.1]heptane, 2,5-diazabicyclo[2.2.1]heptane, and 2,3,4,4a,9,9a-hexahydro-1H-β-carboline.

In the above methods, A and X in any of the above compounds may independently be halo or $NR^1R^2$, where $R^1$ is H and $R^2$ is a $C_{1-10}$ alkyl substituted with morpholine, thiomorpholine, imidazole, aminodithiadiazole, pyrrolidine, piperazine, pyridine or piperidine. Alternatively, $R^1$ and $R^2$ together with N may form with N piperidine, pyrrolidine, piperazine, morpholine, thiomorpholine, imidazole, or aminodiathiazole.

Alternatively, X in any of the above compounds may be an amine moiety having the formula

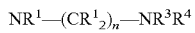

wherein $R^1$ and $R^3$ are independently H or $C_{1-6}$ alkyl;
n is 1-6; and
$R^4$ is H or a $C_{1-10}$ alkyl or $C_{2-10}$ alkenyl optionally containing one or more non-adjacent heteroatoms selected from N, O and S, and optionally substituted with a carbocyclic or heterocyclic ring; and
wherein in $NR^3R^4$, $R^3$ and $R^4$ may form an optionally substituted ring.

In the above amine moiety, n may be 2-3. In one example, $R^3$ and $R^4$ in $NR^3R^4$ together form an optionally substituted ring containing one or more N, O or S.

In some embodiments, A, V, B and X, when present, are all H. In other embodiments, three of A, V, B and X are H. In other embodiments, two of A, V, B and X are H. In yet other embodiments, only one of A, V, B and X is H. In certain embodiments, only one of A, V, B and X is a halogen (e.g., fluorine). In other embodiments, two of A, V, B and X are halogen. In still other embodiments, three of A, V, B and X are halogen.

In the above methods, each optionally substituted moiety in any of the above compounds may be substituted with one or more halo, $OR^2$, $NR^1R^2$, carbamate, $C_{1-10}$ alkyl, $C_{2-10}$ alkenyl, each optionally substituted by halo, C=O, aryl or one or more heteroatoms; inorganic substituents, aryl, carbocyclic or a heterocyclic ring.

In certain embodiments, a compound of any one of the formulae above may have the following substituents:

each of A, V and B is independently H or halogen (e.g., chloro or fluoro);

X is —$(R^5)R^1R^2$, wherein $R^5$ is C or N and wherein in each —$(R^5)R^1R^2$, $R^1$ and $R^2$ together may form an optionally substituted aryl or heteroaryl ring;

Z is NH or N-alkyl (e.g., N—$CH_3$);

W in formula 1 or 2 is an optionally substituted aryl or heteroaryl ring; and $R^2$ is —$CHR^1$—$NR^3R^4$, wherein each $R^3$ or $R^4$ together with the C may form an optionally substituted heterocyclic or heteroaryl ring, or wherein each $R^3$ or $R^4$ together with the N may form an optionally substituted carbocyclic, heterocyclic, aryl or heteroaryl ring.

The methods of the present invention are illustrated as shown in Scheme 1 and in the Examples. The present method encompasses variations in the methods known to those with ordinary skill in the art. For example, various protecting groups may be used in the preparation of the intermediate illustrated in Side-Chain 1. (See, e.g., Example 11.)

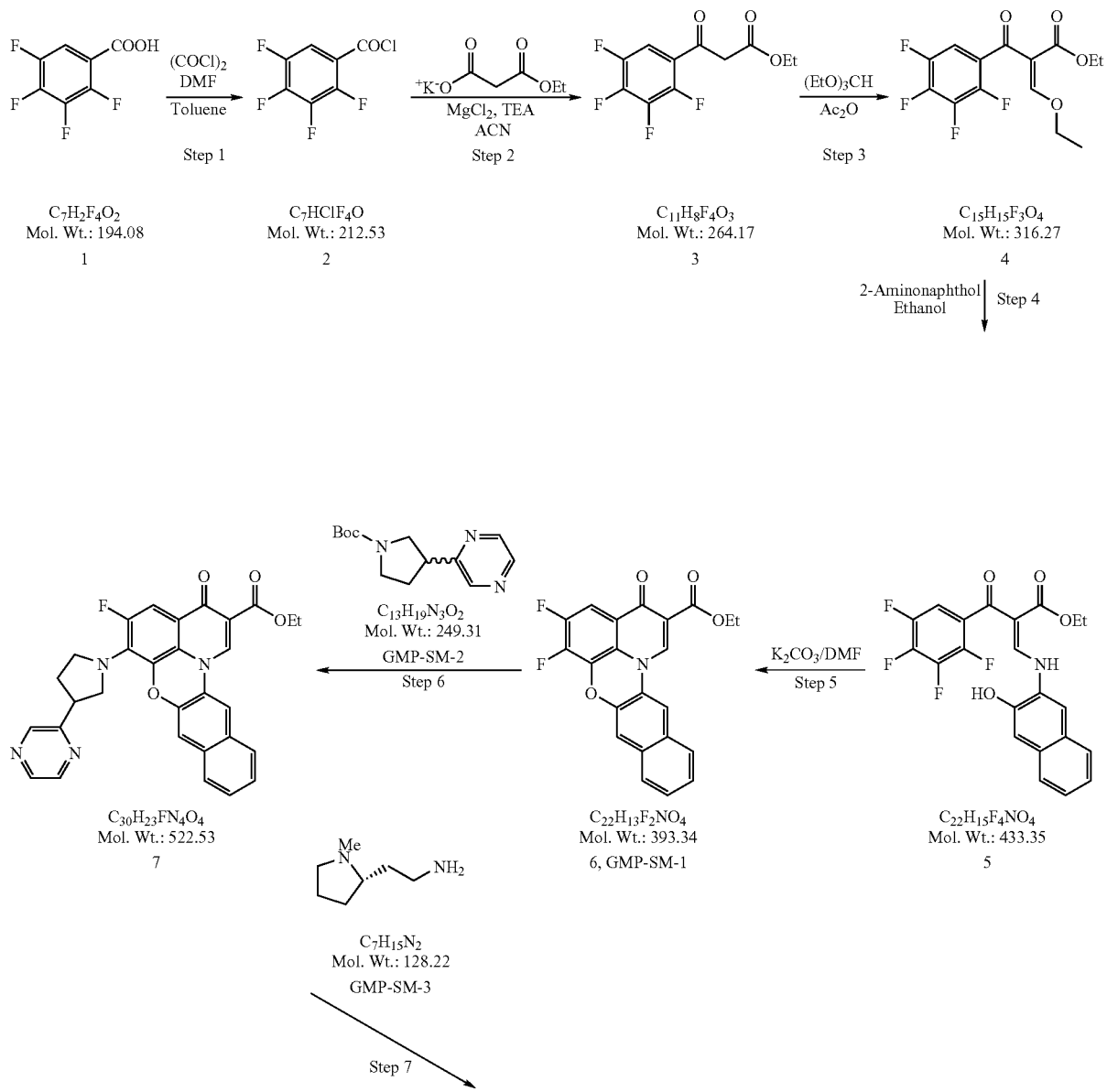

Scheme 1

-continued

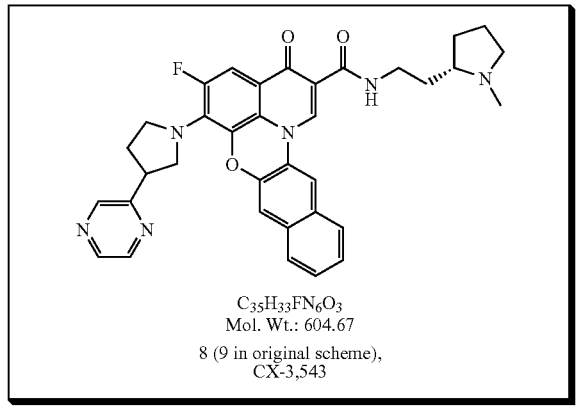

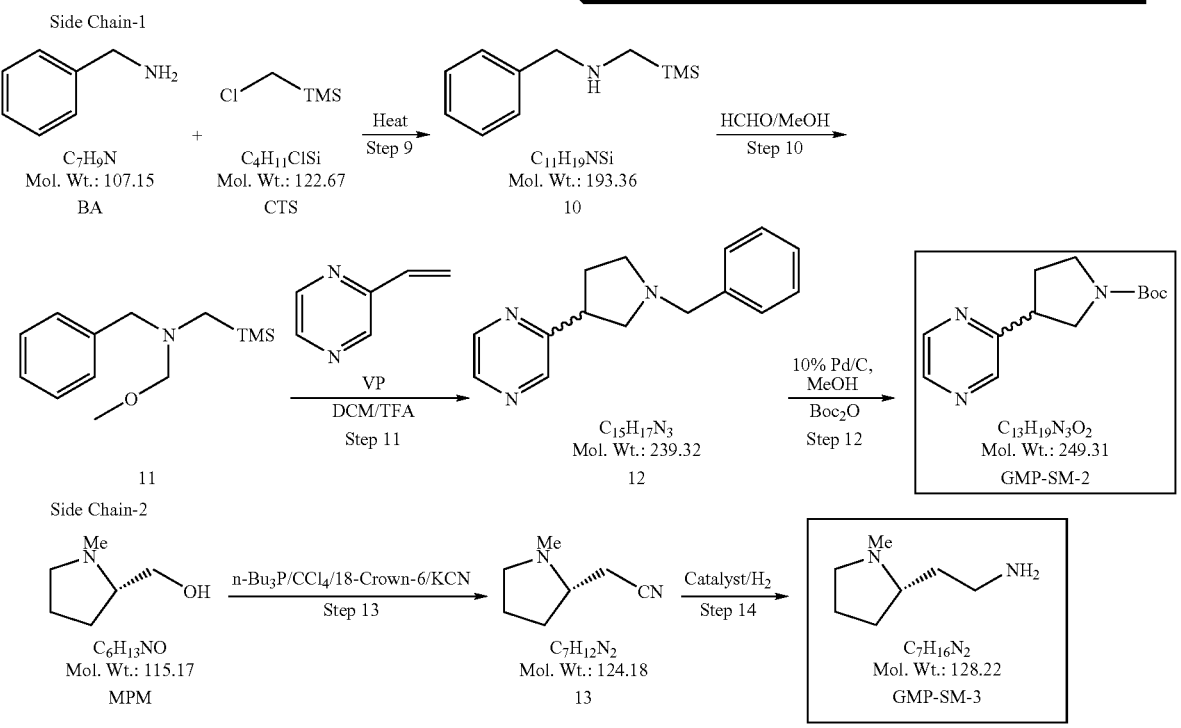

The compounds prepared according to the methods of the present invention may interact with regions of DNA that can form quadruplexes and act as tumor suppression genes with high affinity. Furthermore, the compounds may induce cell death (e.g., apoptosis), and not interact with regions of DNA that can form quadruplexes. Such compounds may reduce expression of highly proliferate genes and may be utilized to treat a cell proliferative disorder such as a tumor or cancer. Furthermore, the compounds may also exhibit antibacterial or antiviral activity, and may be used for treating bacterial and viral infections.

The compounds of the present invention may be chiral. As used herein, a chiral compound is a compound that is different from its mirror image, and has an enantiomer. Furthermore, the compounds may be racemic, or an isolated enantiomer or stereoisomer. Methods of synthesizing chiral compounds and resolving a racemic mixture of enantiomers are well known to those skilled in the art. See, e.g., March, "*Advanced Organic Chemistry*," John Wiley and Sons, Inc., New York, (1985), which is incorporated herein by reference.

Definitions

As used herein, the term "alkyl" refers to a carbon-containing compound, and encompasses compounds containing one or more heteroatoms. The term "alkyl" also encompasses alkyls substituted with one or more substituents including but not limited to $OR^1$, amino, amido, halo, =O, aryl, heterocyclic groups, or inorganic substituents.

As used herein, the term "carbocycle" refers to a cyclic compound containing only carbon atoms in the ring, whereas a "heterocycle" refers to a cyclic compound comprising a heteroatom. The carbocyclic and heterocyclic structures encompass compounds having monocyclic, bicyclic or multiple ring systems.

As used herein, the term "aryl" refers to a polyunsaturated, typically aromatic hydrocarbon substituent, whereas a "heteroaryl" or "heteroaromatic" refer to an aromatic ring containing a heteroatom. The aryl and heteroaryl structures encompass compounds having monocyclic, bicyclic or multiple ring systems.

As used herein, the term "heteroatom" refers to any atom that is not carbon or hydrogen, such as nitrogen, oxygen or sulfur.

As used herein, the term "Lewis acid" refers to any species that can accept an electron pair, such as metal ions and electron-deficient molecules. In one example, the methods of the present invention use a strong Lewis acid such as aluminum chloride. Other Lewis acids may be used in practicing the methods of the present invention, including species having the formula $ML_n$, wherein L is a halogen atom or an organic radical such as an alkyl group, n is 3-5, and M is a group III elemental atom (e.g., B, Al, Ga, In), or a group IV elemental atom (e.g., Zr, Ti, Sn). Strong Lewis acidity is also observed for certain group V elemental atoms (e.g., As, Sb, V), and group VIII elemental atoms (e.g. Fe). Group II elemental atoms (e.g., Zn, Cd) generally display moderate Lewis acidity. Particular Lewis acids that may be used to practice the methods of the present invention include but are not limited to: $BL_3$; $AlL_3$; $FeL_3$; $GaL_3$; $SbL_5$; $InL_3$; $ZrL_4$; $SnL_4$; $TiL_4$; $TiL_3$; $AsL_3$; $SbL_3$. (See, e.g., D. P. N. Satchell & R. S. Satchell, *Quantitative Aspects of the Lewis Acidity of Covalent Metal Halides and their Organo Derivatives,* 69 CHEM. REV. 251, 253-55 (1969)).

Illustrative examples of heterocycles include but are not limited to tetrahydrofuran, 1,3-dioxolane, 2,3-dihydrofuran, pyran, tetrahydropyran, benzofuran, isobenzofuran, 1,3-dihydro-isobenzofuran, isoxazole, 4,5-dihydroisoxazole, piperidine, pyrrolidine, pyrrolidin-2-one, pyrrole, pyridine, pyrimidine, octahydro-pyrrolo[3,4-b]pyridine, piperazine, pyrazine, morpholine, thiomorpholine, imidazole, imidazolidine-2,4-dione, 1,3-dihydrobenzimidazol-2-one, indole, thiazole, benzothiazole, thiadiazole, thiophene, tetrahydrothiophene 1,1-dioxide, diazepine, triazole, guanidine, diazabicyclo[2.2.1]heptane, 2,5-diazabicyclo[2.2.1]heptane, 2,3,4,4a,9,9a-hexahydro-1H-β-carboline, oxirane, oxetane, tetrahydropyran, dioxane, lactones, aziridine, azetidine, piperidine, lactams, and may also encompass heteroaryls. Other illustrative examples of heteroaryls include but are not limited to furan, pyrrole, pyridine, pyrimidine, imidazole, benzimidazole and triazole.

DESCRIPTION OF THE INVENTION

The following examples are offered to illustrate but not to limit the invention.

EXAMPLE 1

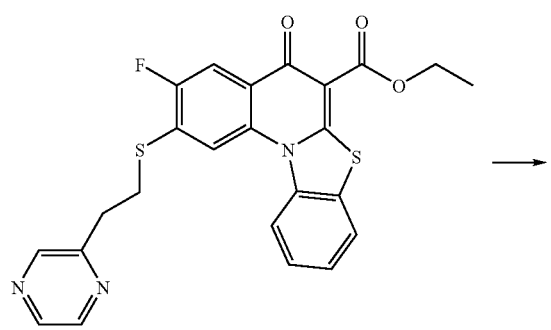

To a solution of the quinolone ester (60 mg, 0.13 mmol) and 2-(2-aminoethyl)-1-methyl pyrrolidine (30 μL, 0.19 mmol) in methylene chloride (1.0 mL) was added aluminum chloride (25 mg, 0.19 mmol) and the reaction mixture was allowed to stir for 30 minutes. The solvent was removed in vacuo and saturated L-tartaric acid (1.0 mL) was added, stirring for 45 minutes, until all of the solid dissolved. The aqueous solution was washed with methylene chloride (1.0 mL), basified with 1N NaOH and extracted with methylene chloride. The resulting extract was washed with brine, dried over sodium sulfate, filtered and the solvent was removed in vacuo. The resulting yellow material was purified on preparative TLC (Alumina, 2% Methanol in $CH_2Cl_2$) to afford the product as a yellowish solid (30 mg, 43%).

EXAMPLE 2

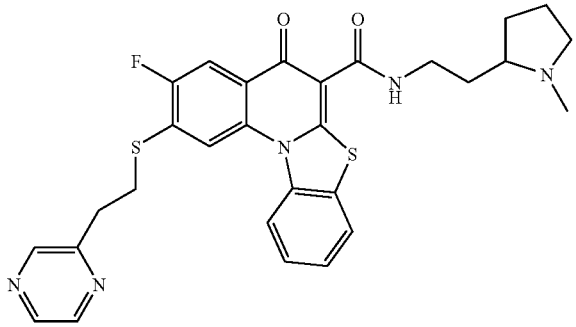

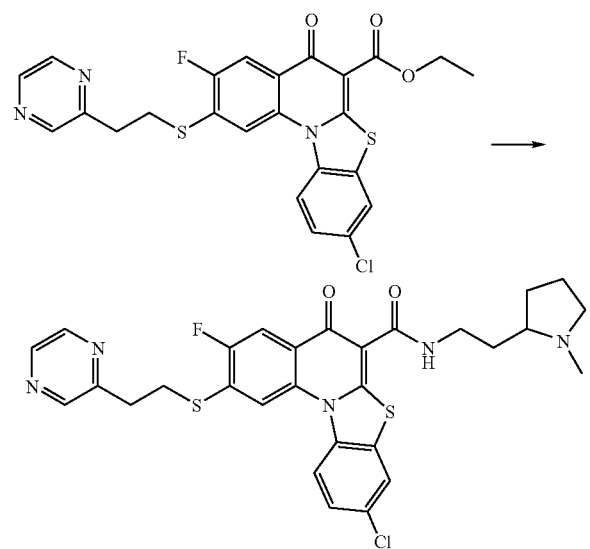

To a solution of the quinolone ester (60 mg, 0.11 mmol) and 2-(2-aminoethyl)-1-methylpyrrolidine (25 μL, 0.17 mmol) in methylene chloride (1.0 mL) was added aluminum chloride (23 mg, 0.17 mmol) and the reaction mixture was allowed to stir for 30 minutes. The solvent was removed in vacuo and saturated L-tartaric acid (1.0 mL) was added, stirring for 45 minutes, until all of the solid dissolved. The aqueous solution was washed with methylene chloride (1.0 mL), basified with 1N NaOH and extracted with methylene chloride. The resulting extract was washed with brine, dried over sodium sulfate, filtered and the solvent was removed in vacuo. The resulting yellow material was purified on preparative TLC (Alumina, 2% Methanol in CH$_2$Cl$_2$) to afford the product as a yellowish solid (30 mg, 46%).

EXAMPLE 3

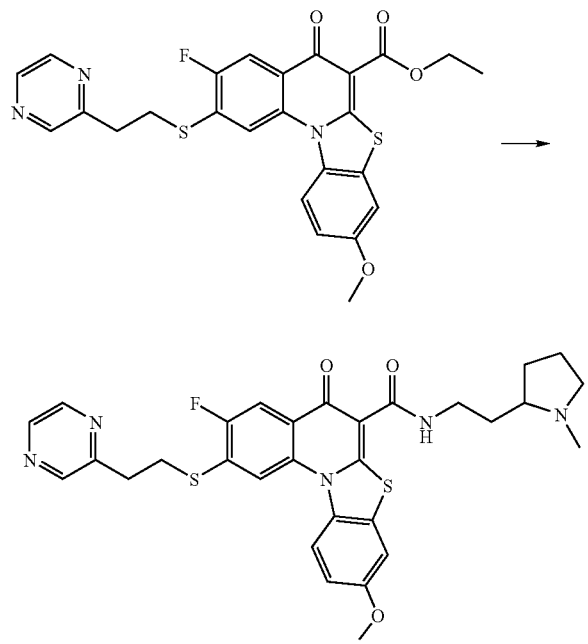

To a solution of the quinolone ester (75 mg, 0.15 mmol) and 2-(2-aminoethyl)-1-methylpyrrolidine (32 µL, 0.22 mmol) in methylene chloride (1.0 mL) was added aluminum chloride (29 mg, 0.22 mmol) and the reaction mixture was allowed to stir for 30 minutes. The solvent was removed in vacuo and saturated L-tartaric acid (1.0 mL) was added, stirring for 45 minutes, until all of the solid dissolved. The aqueous solution was washed with methylene chloride (1.0 mL), basified with 1N NaOH and extracted with methylene chloride. The resulting extract was washed with brine, dried over sodium sulfate, filtered and the solvent was removed in vacuo. The resulting yellow material was purified on preparative TLC (Alumina, 2% Methanol in CH$_2$Cl$_2$) to afford the product as a yellowish solid (30 mg, 34%).

EXAMPLE 4

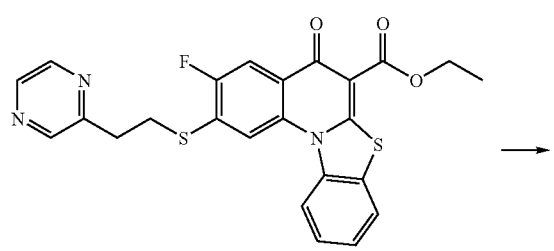

-continued

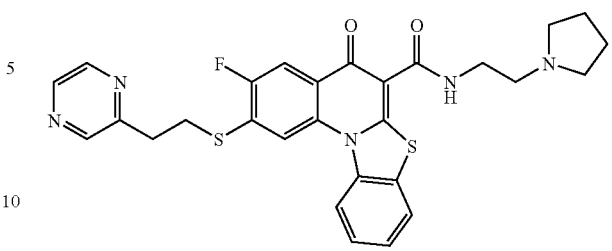

To a solution of the quinolone ester (34 mg, 0.7 mmol) and 1-(2-aminoethyl) pyrrolidine (15 µL, 0.11 mmol) in methylene chloride (1.0 mL) was added aluminum chloride (15 mg, 0.11 mmol) and the reaction mixture was allowed to stir for 30 minutes. The solvent was removed in vacuo and saturated L-tartaric acid (1.0 mL) was added, stirring for 45 minutes, until all of the solid dissolved. The aqueous solution was washed with methylene chloride (1.0 mL), basified with 1N NaOH and extracted with methylene chloride. The resulting extract was washed with brine, dried over sodium sulfate, filtered and the solvent was removed in vacuo. The resulting yellow material was purified on preparative TLC (Alumina, 2% Methanol in CH$_2$Cl$_2$) to afford the product as a yellowish solid (28 mg, 73%).

EXAMPLE 5

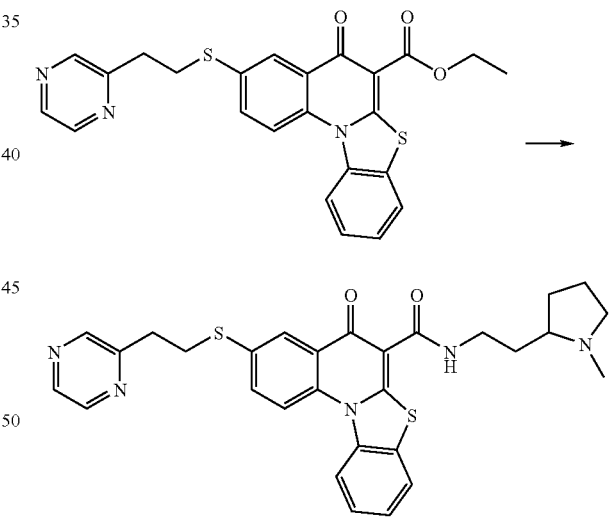

To a solution of the quinolone ester (146 mg, 0.65 mmol) and 2-(2-aminoethyl)-1-methylpyrrolidine (1 mmol) in methylene chloride (1.0 mL) was added aluminum chloride (1 mmol) and the reaction mixture was allowed to stir for 30 minutes. The solvent was removed in vacuo and saturated L-tartaric acid (1.0 mL) was added, stirring for 45 minutes, until the entire solid dissolved. The aqueous solution was washed with methylene chloride (1.0 mL), basified with 1N NaOH and extracted with methylene chloride. The resulting extract was washed with brine, dried over sodium sulfate, filtered and the solvent was removed in vacuo. The resulting yellow material was purified on preparative TLC (Alumina, 2% Methanol in $CH_2Cl_2$) to afford the product as a yellowish solid (1.7 mg, 5%).

EXAMPLE 6

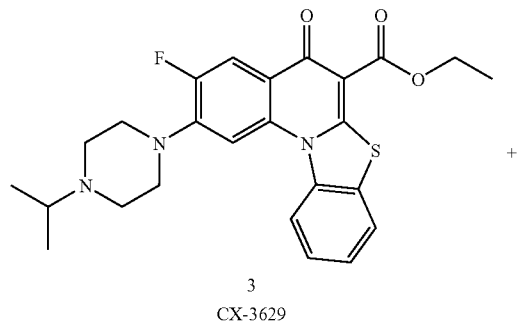

3
CX-3629

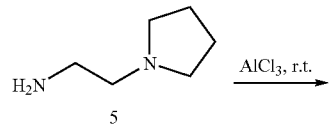

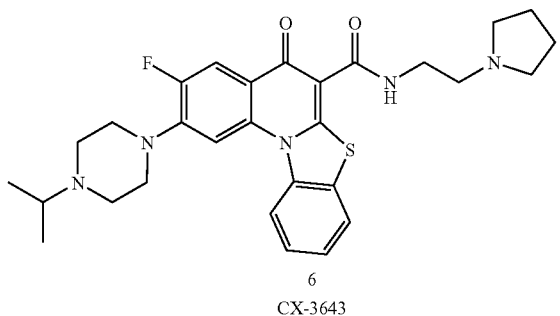

6
CX-3643

CX-3629 3 (1.0 eq, 126 mg, 0.27 mmol) and amine 5 (2.0 eq, 68 µL, 0.54 mmol) were dissolved in anhydrous $CH_2Cl_2$ (1 ml). $AlCl_3$ (2.0 eq, 72 mg, 0.54 mmol) was added and the mixture was stirred at room temperature for 3 hours. The volatiles were removed in vacuo. The resulting slurry was treated with a saturated aqueous tartaric acid solution (10 ml) and stirred until all solid disappeared (about 1 hr for completion of the hydrolysis). The solution was neutralized by 1N NaOH (to reach pH=14) and the compound extracted with $CH_2Cl_2$ (4x). The organic phase was washed with a concentrated aqueous Sodium Potassium tartrate solution, water (2x) and dried over $Na_2SO_4$. The $CH_2Cl_2$ solution was concentrated. Addition of AcOEt induced crystallization of the expected compound. After filtration CX-3643 6 was isolated as a pale yellow fluffy solid (76 mg, 53% yield). LCMS (ES): 95% pure, m/z 536 [M+H]$^+$; $^1$H NMR (CDCl$_3$, 500 MHz) δ 1.12 (d, J=6.6, 6H), 1.80 (br s, 4H), 2.62 (br s, 4H), 2.79 (m, 7H), 3.36 (m, 4H), 3.67 (q, J=6.0, 2H), 7.45 (t, J=7.2, 1H), 7.53 (td, J=7.3, J=1.3, 1H), 7.84 (dd, J=7.8, J=1.2, 1H), 7.89 (d, J=6.9, 1H), 8.16 (d, J=13.1, 1H), 8.23 (d, J=8.5, 1H), 10.46 (br t, 1H) ppm.

EXAMPLE 7

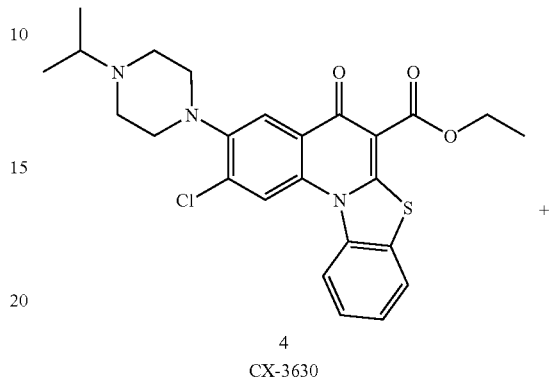

4
CX-3630

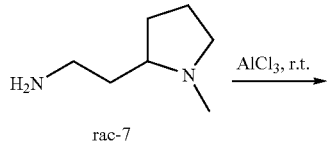

rac-7

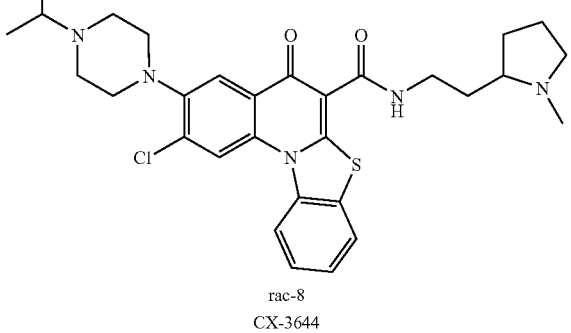

rac-8
CX-3644

The compound was prepared according to the procedure used for CX-3643, starting from 4 (101 mg, 0.21 mmol) and 7, providing CX-3644 8 as a white fluffy solid (37 mg, 31% yield). LCMS (ES): 95% pure, m/z 566 [M]$^+$, 568 [M+2]$^+$; $^1$H NMR (CDCl$_3$, 500 MHz) δ 1.13 (d, J=6.5, 6H), 1.57 (m overlapped with water signal, 2H), 1.71 (m, 1H), 1.81 (m, 1H), 2.04-2.18 (m, 4H), 2.34 (s, 3H), 2.78 (m, 5H), 3.06 (br t, J=8.6, 1H), 3.27 (br s, 4H), 3.52-3.59 (m, 2H), 7.47 (t, J=7.3, 1H), 7.57 (td, J=8.4, J=1.1, 1H), 7.84 (d, J=7.8, 1H), 8.19 (s, 1H), 8.27 (d, J=8.4, 1H), 8.57 (s, 1H), 10.38 (br t, J=5.6, 1H) ppm.

EXAMPLE 8

Example 8 describes a method for preparing a substituted benzoxazine analog from reaction of the corresponding ester with an amine, and aluminum chloride.

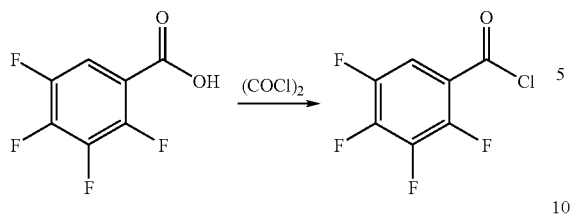

To a solution of 2,3,4,5-tetrafluorobenzoic acid (100 g, 510 mmol), in methylene chloride (0.5 L) was added oxalyl chloride (68 g, 540 mmol) and DMF (ca 3 drops) and the reaction mixture was allowed to stir at room temperature overnight allowing for the produced gasses to escape. The solvent was removed in vacuo and the vessel was placed on high vacuum (ca 0.5 mm Hg) for 2 hours to afford the acid chloride as a viscous oil (105 g) and was used in the subsequent reaction without further purification.

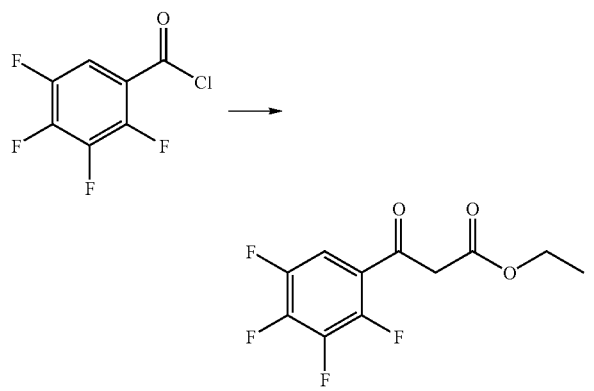

To a suspension of potassium ethyl malonate (97 g, 570 mmol) and magnesium chloride (55 g, 570 mmol) in acetonitrile and the suspension was chilled to 0° C. To this suspension was added the crude 2,3,4,5-benzoyl chloride (105 g, 520 mmol) over 5 minutes. Triethylamine was slowly added at a rate sufficient to keep the reaction temperature below 10° C. and the mixture was allowed to warm to room temperature and was stirred overnight. The solvent was removed in vacuo and replaced with toluene (300 mL) and 1N HCl (500 mL) was added and the mixture was allowed to stir for 1 hour. The organic layer was separated and washed with 1N HCl (100 mL) and brine (100 mL) and dried over sodium sulfate, filtering over a pad of silica gel (50×100 mm), eluting with ethyl acetate. The solvent was removed in vacuo and the resulting oil was dissolved in ethanol/water (9:1) and was allowed to crystallize overnight. The resulting crystals were Isolated by filtration, washing with ethanol/water (8:2) to afford the ketoester (43.75 g, 166 mmol) as a white crystalline solid.

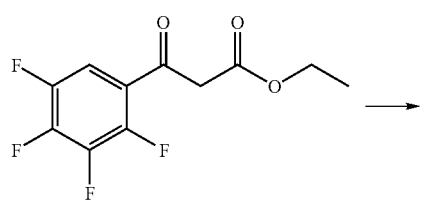

-continued

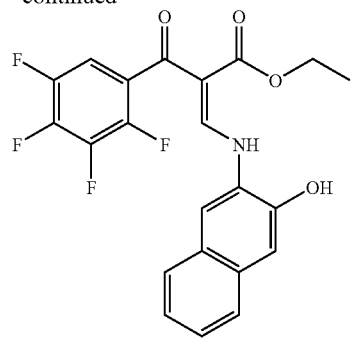

To a 250 mL round bottom flask was added the tetrafluoroketoester (10.0 g, 37.9 mmol), triethylorthoformate (8.6 mL, 56.8 mmol) and acetic anhydride (7.15 mL, 75.8 mmol) and the reaction mixture was heated to 145° C. for 2 hours. The reaction was allowed to cool to room temperature and placed on high vacuum (ca 0.5 mm Hg) for 1 hour. The resulting oil was dissolved in ethanol (100 mL) and 2-amino-1-naphthol (6.02 g, 37.9 mmol) was added at room temperature and the solution became briefly clear and then product began to precipitate. The reaction was allowed to stir for 2 hours and was then filtered and washed with ethanol (100 mL) to afford the enamine as a yellow solid (12.5 g, 28.9 mmol).

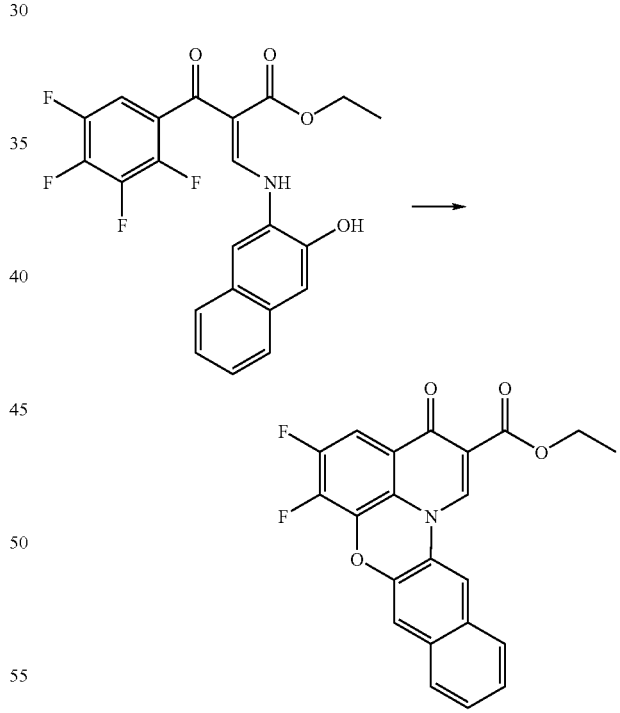

To a solution of the enamine (12.13 g, 27.95 mmol) in dry DMF (50 mL) was added potassium carbonate (4.24 g, 1.1 eq.) and the mixture was heated to 90° C., with constant stirring, for 2 hours. The mixture was allowed to cool to room temperature without stirring and was allowed to remain at room temperature for an additional hour. The crystalline solid was collected by filtration, washing with water. Recrystallization from THF afforded the difluoroester as a white crystalline solid (9.3 g, 23.6 mmol).

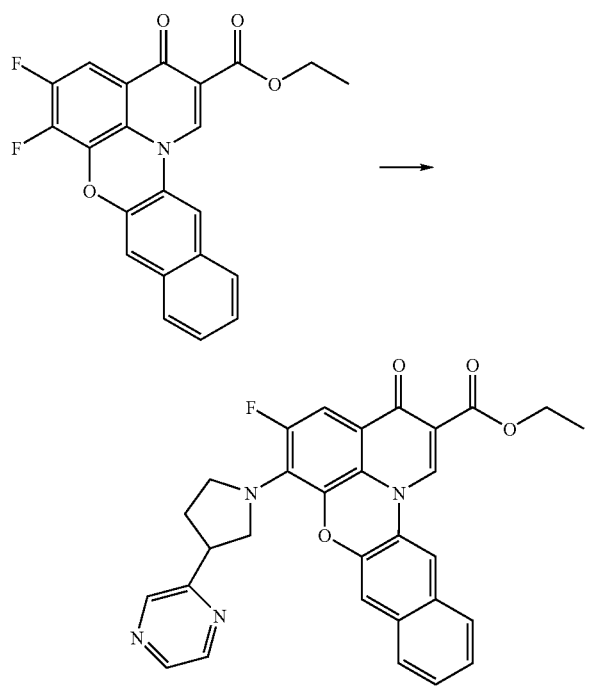

To a solution of the difluoroester (11.0 g, 2.5 mmol) in NMP (10 mL) was added N-Boc-3-(2-pyrazino)pyrrolidine (870 mg, 3.5 mmol) and the mixture was heated to reflux for 3 hours. The reaction mixture was then allowed to cool to room temperature and the product was collected by filtration. Crystallization from THF afforded the pyrazine ester as a yellow solid (910 mg, 1.74 mmol).

To a solution of the pyrazine ester (250 mg, 0.48 mmol) and 2-(2-aminoethyl)-1-methylpyrrolidine (80 mg, 0.63 mmol) in methylene chloride at room temperature was added aluminum chloride (83 mg, 0.63 mmol) and the reaction mixture was allowed to stir for 2 hours. The solvent was removed in vacuo and saturated L-tartaric acid was added (5 mL) and the mixture was allowed to stir for 1 hour. Methylene chloride (10 mL) was then added and the mixture was basified with 1N NaOH. The organic layer was separated and washed with a saturated solution of Rochelle's salt, brine and dried over sodium sulfate. The solvent was removed in vacuo and the resulting solid was dissolved in THF and filtered and the solvent was removed again. The crude solid was recrystallized in ethyl acetate to afford the amide as a yellow solid (225 mg, 0.37 mmol, 98.5% pure).

EXAMPLE 9

As shown in Example 9, amide coupling from the corresponding ester resulted in slight or no reaction, where zinc chloride was used as the Lewis acid.

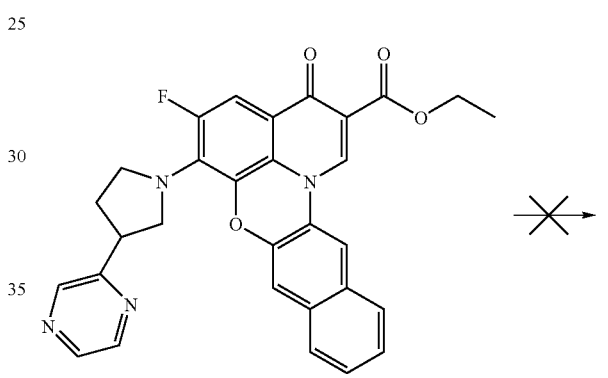

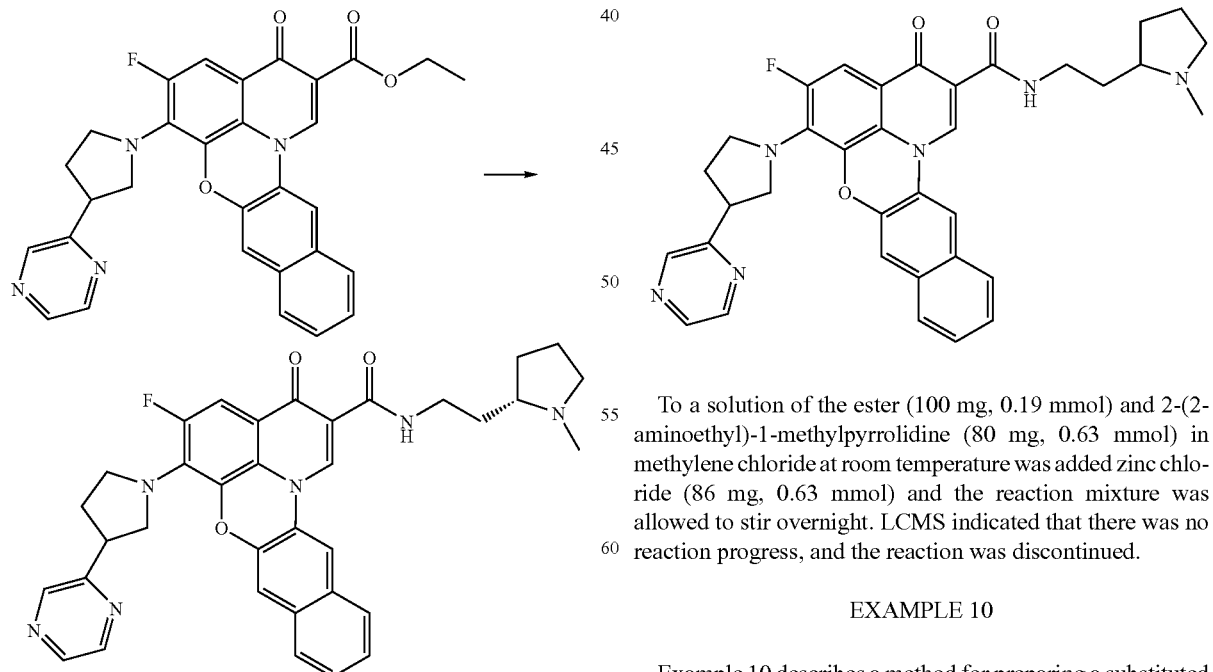

To a solution of the ester (100 mg, 0.19 mmol) and 2-(2-aminoethyl)-1-methylpyrrolidine (80 mg, 0.63 mmol) in methylene chloride at room temperature was added zinc chloride (86 mg, 0.63 mmol) and the reaction mixture was allowed to stir overnight. LCMS indicated that there was no reaction progress, and the reaction was discontinued.

EXAMPLE 10

Example 10 describes a method for preparing a substituted benzoxazine analog from reaction of the corresponding carboxylic acid with an amine.

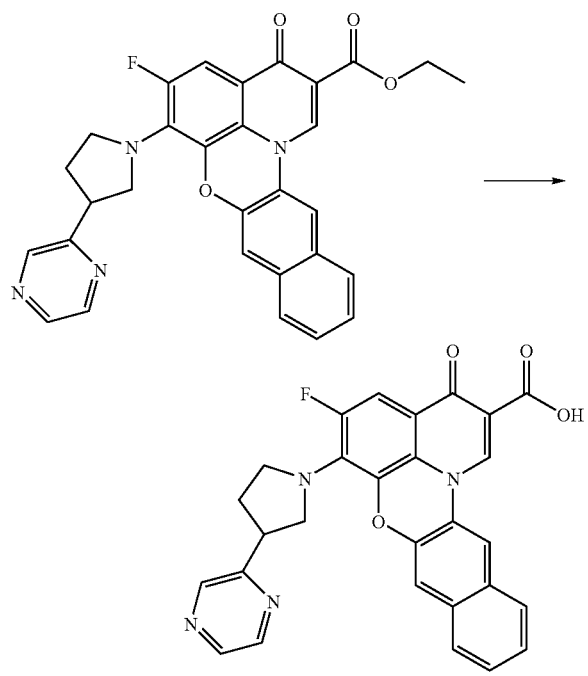

The pyrazinoester (2.0 g, 3.8 mmol) was dissolved in ethanol (100 mL) and conc HCl was added (20 mL) and the mixture was refluxed overnight. The mixture was allowed to cool to room temperature and the solid was collected by vacuum filtration, washing with ethanol to afford the pyrazinoacid as a light tan powder (1.6 g, 3.2 mmol).

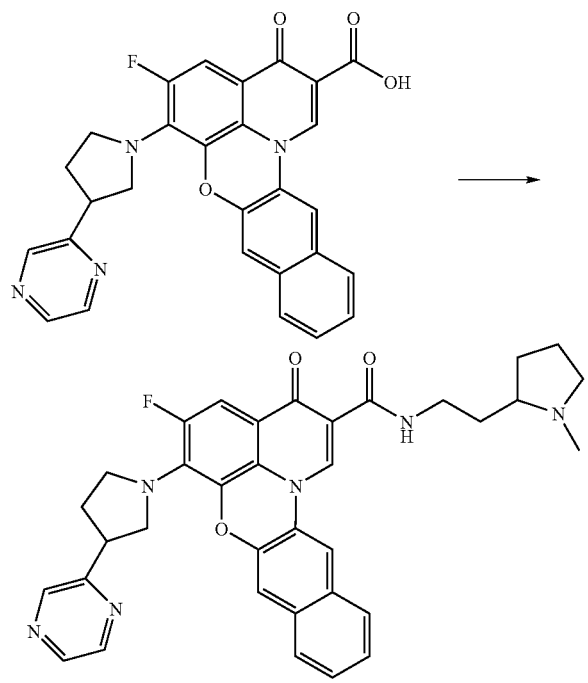

To a mixture of the fluoroaminoacid (1.6 g, 3.2 mmol) and HBTU (2.0 g, 5.3 mmol) in NMP (20 mL) was added N,N-diisopropyl-N-ethylamine (1.0 mL, 6 mmol) and the mixture was allowed to stir at room temperature, under argon, for 1 hour (the solution became clear). (S)-2-(2-aminoethyl)-1-methylpyrrolidine (Mizuno, A.; Hamada, Y.; Shioiri, T., Synthesis, 1980, 12 1007)(1.0 mL, 6.9 mmol) was added and the mixture was allowed to stir for 30 minutes. Water (200 mL) was added and the resulting solid was collected by vacuum filtration, washing with water, and dried to afford the pyrazine as a yellow solid. The yellow solid was purified on silica gel (10% MeOH/CH$_2$Cl$_2$ first eluting off impurities followed by eluting with 5% NH$_4$OH/15% MeOH/CH$_2$Cl$_2$. The combined fractions were evaporated to afford the compound as a yellow solid. (1.2 g, 2.0 mmol, 85% pure).

EXAMPLE 11

Example 11 describes the preparation of a Boc-protected pyrrolidine reagent, used as an intermediate in the preparation of benzoxazine and benzothiazole compounds.

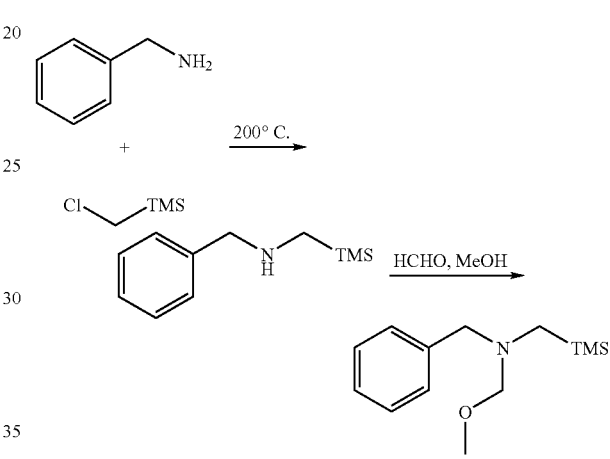

A mixture of benzyl amine (90 g, 841 mmol) and chloromethyltrimethylsilane (30 g, 246 mmol) was heated at 200° C. for 2.5 hours. In general, the trimethylsilyl group may be replaced with a —SiR$^1$R$^2$R$^3$ moiety, wherein R$^1$, R$^2$ and R$^3$ are independently alkyl or substituted alkyl. The benzyl groups may also be replaced with other suitable protecting groups.

The mixture was allowed to cool to room temperature and treated with 1N sodium hydroxide (250 mL) and ether (200 mL) with stirring. The aqueous layer was extracted with ether (3×100 mL) and the combined organic extracts were washed with brine, dried over magnesium sulfate and filtered over a pad of silica gel (70×50 mm), eluting with ether. The solvent was removed in vacuo and the resulting oil was vacuum distilled (bp=70° C. ca 1 mm Hg) to afford the amine as a colorless oil (60.8 g) that contained a significant amount of benzyl amine. The resulting oil was then chromatographed on a single biotage column (90 g, silica gel, ANALOGIX) eluting with ethyl acetate. The solvent was removed in vacuo to afford the pure amine as a colorless oil (43.55 g, 225 mmol). The resulting amine was then added to 37% formalin (25 mL) and the mixture was stirred at room temperature for 10 minutes, followed by the addition of methanol (25 mL) and potassium carbonate (20 g). The resulting mixture was allowed to stir overnight and then extracted with methylene chloride (3×100 mL) and the combined organic extracts were dried with sodium sulfate. The solvent was removed in vacuo and the resulting oil was vacuum distilled (bp=80° C. ca 1 mm Hg) to afford the amine as a colorless liquid (39.9 g, 168 mmol).

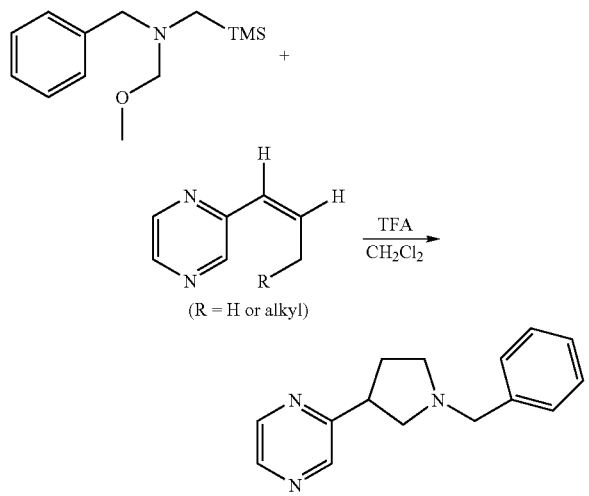

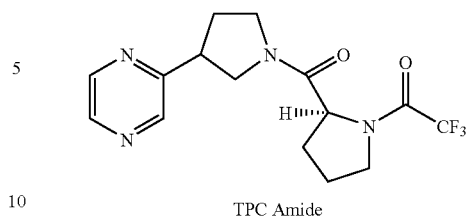

TPC Amide

Enantiomeric ratios can be determined by making a TPC (N-trifluoromethylacetyl-L-prolyl chloride, Regis #440001) and using GCMS (HP 6890N/5973 MSD) on a Phenomenex Zebron capillary column (ZB-50, 50% Phenyl, 50% Diemthylpolysiloxane, 30M×0.25 mm, 0.25 uM film thickness). Chromatography conditions: 1 μL injection split 50:1. Constant Flow He=1.0 mL/min. Oven; 100° C. for 5 min, 5° C./min to 300° C. and hold for 8 minutes. The compound comes at 39.08 and 39.31 min but the resolution is very good.

To a solution of vinylpyrazine (10 g, 94.3 mmol) in methylene chloride (200 mL) and trifluoroacetic acid (2 mL) was added dropwise a solution of the silylated amine ether (24.33 g, 102.7 mmol) dissolved in methylene chloride (100 mL) over 4 hours. The volume was then reduced to 100 mL and extracted with 1N HCl (3×75 mL). The aqueous layer was then basified with NaOH and extracted with methylene chloride (3×100 mL), dried over magnesium sulfate and filtered over a pad of silica gel (30×150 mm) eluting with ethyl acetate. The solvent was evaporated to afford the benzylated pyrazinopyrrolidine (26.19 g) as a brownish clear liquid. In general, the pyrazine heterocycle may be replaced with other suitable heterocyclic groups.

EXAMPLE 12

Example 12 describes the preparation of a chiral amine reagent used in amide coupling.

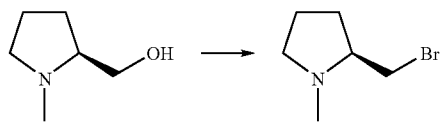

To a solution of the hydroxymethylpyrrolidine (50 g, 434 mmol) in methylene chloride (1 L) was added triphenylphosphine (148 g, 564 mmol) followed by careful addition of carbon tetrabromide (187 g, 564 mmol) at room temperature. The reaction mixture was allowed to stir for 1 hour at room temperature. Water was added and the organic layer was washed with brine, dried over sodium sulfate and the solvent was removed in vacuo. The resulting oil was purified by silica gel chromatography (1:1 hexanes/ethyl acetate) to afford the bromide as a clear oil (35 g, 197 mmol).

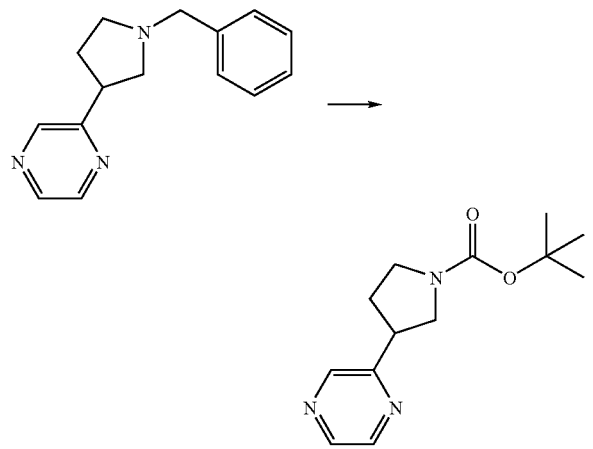

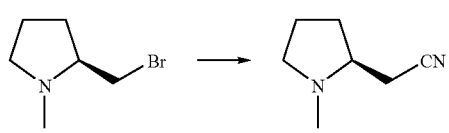

To a solution of the benzyl pyrrolidine (7.0 g, 29.3 mmol) and di-tert-butyldicarbonate (44.7 g, 205 mmol) in methanol (35 mL) was added 10% Pd/C (degussa type, wet) and the vessel was pressurized with Hydrogen (50 PSI) with shaking. The vessel was vented 3 times to control pressure. After 5 hours the reaction was complete and the mixture was filtered and the solvent was removed in vacuo. The resulting material was chromatographed on silica gel (1:1 hexanes/ethyl acetate) to afford the Boc protected pyrrolidine as a light yellow oil (2.3 g, 9.2 mmol).

To a solution of the bromide (23.0 g, 129 mmol) in a solution of acetonitrile and water (75:15, 200 mL) was added potassium cyanide (12.6 g, 194 mmol) and 18-crown-6 (340 mg, 1.3 mmol) and the reaction was allowed to stir overnight at room temperature. The volume was then reduced to 50 mL, under vacuum, and was extracted twice with methylene chloride (2×200 mL). The resulting extracts were combined and washed with brine, dried over sodium sulfate and the solvent was carefully removed in vacuo to afford the cyanide as a clear oil (17 g).

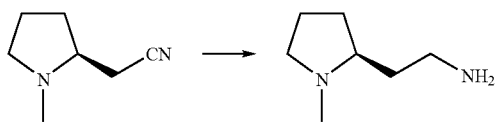

To a solution of the cyanide (17 g, 137 mmol) in methanol (90 mL) was added Raney Nickel (2.0 g, water solution) and the mixture was pressurized with hydrogen (60 PSI) with shaking for 24 hours. The solution was filtered and the solvent was removed in vacuo. The pure amine was isolated by distillation (BP=50° C., ca 10 mm Hg) as a clear oil (7.54 g, 58.9 mmol).

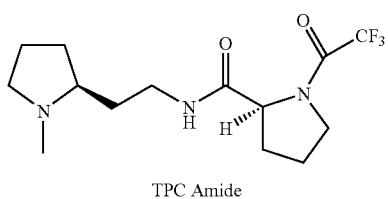

TPC Amide

Enantiomeric ratios can be determined by making a TPC (N-trifluoromethylacetyl-L-prolyl chloride, Regis #440001) and using GCMS (HP 6890N/5973 MSD) on a Phenomenex Zebron capillary column (ZB-50, 50% Phenyl, 50% Diemthylpolysiloxane, 30M×0.25 mm, 0.25 uM film thickness). Chromatography conditions: 1 μL injection split 50:1. Constant Flow He=1.0 mL/min. Oven; 100° C. for 5 min, 5° C./min to 300° C. and hold for 8 minutes. The compound comes at 28.51 and 28.68 min but the resolution is very good.

It is understood that the foregoing detailed description and accompanying examples are merely illustrative, and are not to be taken as limitations upon the scope of the invention. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. U.S. patents and publications referenced herein are incorporated by reference.

What is claimed is:

1. A method for preparing a compound having formula 2,

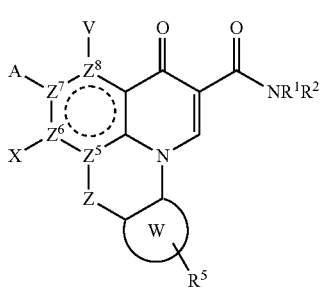

(2)

comprising contacting an ester having formula 4, an amine with formula $NHR^1R^2$ and a Lewis acid having formula $ML_n$, wherein L is a halogen atom or an alkyl group, n is 3-5, and M is a group III elemental atom, a group IV elemental atom, As, Sb, vanadium, or Fe,

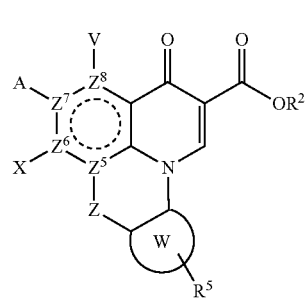

(4)

wherein A, V, and X are independently H, halo, azido, $R^2$, $CH_2R^2$, $SR^2$, $OR^2$ or $NR^1R^2$;

wherein in $NR^1R^2$, $R^1$ and $R^2$ may form an optionally substituted ring; Z is O, S, or $NR^1$;

$Z^5$, $Z^6$, $Z^7$, and $Z^8$ are C;

each $R^1$ is H or a $C_{1-6}$ alkyl;

each $R^2$ is a $C_{1-10}$ alkyl or $C_{2-10}$ alkenyl optionally containing one or more non-adjacent heteroatoms selected from N, O, and S, and optionally substituted with a carbocyclic or heterocyclic ring; or $R^2$ is an optionally substituted carbocyclic ring, heterocyclic ring, aryl or heteroaryl;

each W is an optionally substituted aryl or heteroaryl, which may be monocyclic, or fused with a single or multiple ring and optionally containing a heteroatom;

and each $R^5$ is a substituent at any position on W; and is H, $OR^2$, $NR^1R^2$, $C_{1-6}$ alkyl, $C_{2-6}$ alkenyl, each optionally substituted by halo, C=O or one or more heteroatoms; or two adjacent $R^5$ are linked to obtain a 5-6 substituted or unsubstituted carbocyclic or heterocyclic ring, optionally fused to an additional substituted or unsubstituted carbocyclic or heterocyclic ring.

2. The method of claim 1, wherein said ester, amine, and Lewis acid are contacted at room temperature.

3. The method of claim 1, comprising contacting said ester and amine in an organic solvent to form a solution, and contacting said solution with Lewis acid.

4. The method of claim 3, wherein said organic solvent is methylene chloride.

5. The method of claim 1, wherein an excess of amine in relation to the ester is used.

6. The method of claim 5, wherein the ratio of the ester to the amine is 1:2; 1:1.5; or 1:1.25.

7. The method of claim 1, wherein an equimolar amount of Lewis acid to the amine is used.

8. The method of claim 1, further comprising isolating the compound having formula 2, and optionally purifying said isolated compound having formula 2.

9. The method of claim 8, wherein said isolated compound is purified through column chromatography, recrystallization, or both.

10. The method of claim 9, wherein the purity of the isolated compound is between 90 and 99%.

11. The method of claim 10, wherein the purity of the isolated compound is between 90 and 95%.

12. The method of claim 1, wherein W in any compound having formula 1-4 is selected from the group consisting of:

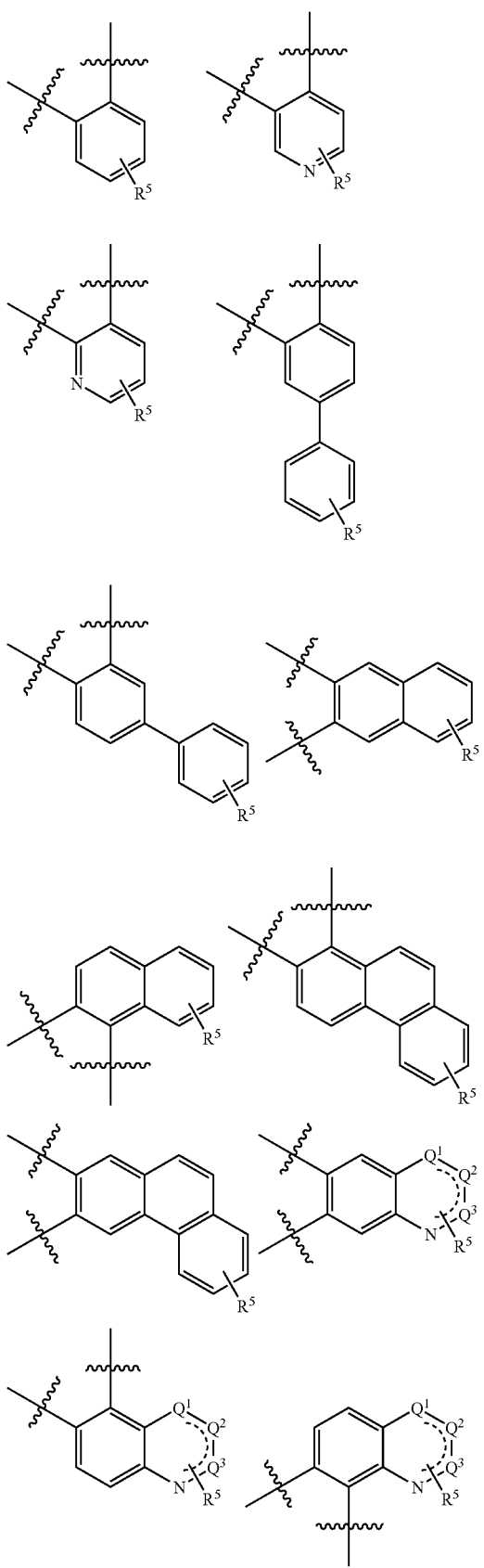
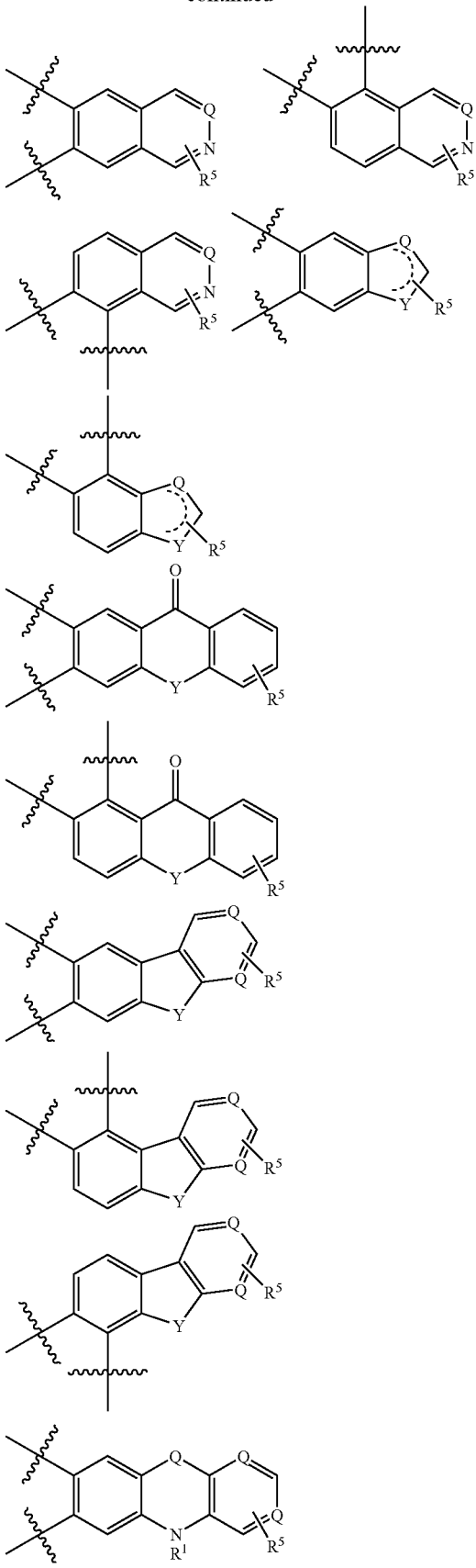

-continued

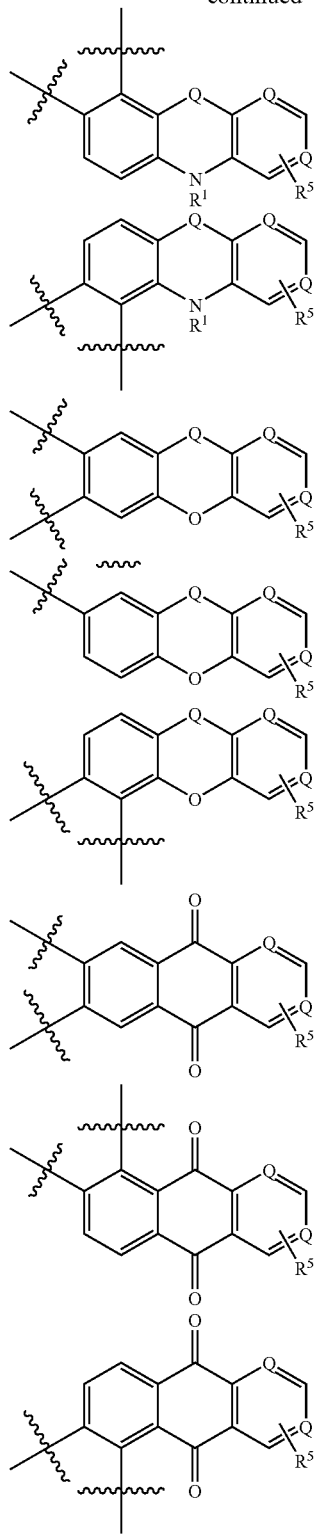

wherein each Q, Q¹, Q², and Q³ is independently CH or N; Y is independently O, CH, C=O or NR¹; and R5 as defined in claim 1.

13. The method of claim 1, wherein X in any compound having formula 2 or formula 4 is SR² where R² is a $C_{1-10}$ alkyl or $C_{2-10}$ alkenyl optionally substituted with a heteroatom, a carbocyclic ring, a heterocyclic ring, an aryl or a heteroaryl.

14. The method of claim 1, wherein X and A in any compound having formula 2 or formula 4 may independently be halo or $NR^1R^2$,
wherein $R^1$ is H;
$R^2$ is a $C_{1-10}$ alkyl optionally substituted with a heteroatom, a $C_{3-6}$ cycloalkyl, aryl or a 5-14 membered heterocyclic ring containing one or more N, O or S;
or $R^1$ and $R^2$ together with N in $NR^1R^2$ may form an optionally substituted heterocyclic ring containing one or more N, O or S.

15. The method of claim 14, wherein $R^2$ is a $C_{1-10}$ alkyl substituted with morpholine, thiomorpholine, imidazole, aminodithiadiazole, pyrrolidine, piperazine, pyridine or piperidine; or wherein $R^1$ and $R^2$ together with N form piperidine, pyrrolidine, piperazine, morpholine, thiomorpholine, imidazole, or aminodithiazole.

16. The method of claim 14, wherein said optionally substituted heterocyclic ring is tetrahydrofuran, 1,3-dioxolane, 2,3-dihydrofuran, tetrahydropyran, benzofuran, isobenzofuran, 1,3-dihydro-isobenzofuran, isoxazole, 4,5-dihydroisoxazole, piperidine, pyrrolidine, pyrrolidin-2-one, pyrrole, pyridine, pyrimidine, octahydro-pynolo[3,4-b]pyridine, piperazine, pyrazine, morpholine, thiomorpholine, imidazole, aminodithiadiazole, imidazolidine-2,4-dione, benzimidazole, 1,3-dihydrobenzimidazol-2-one, indole, thiazole, benzothiazole, thiadiazole, thiophene, tetrahydro-thiophene 1,1-dioxide, diazepine, triazole, guanidine, diazabicyclo [2.2.1]heptane, 2,5-diazabicyclo[2.2.1]heptane, or 2,3,4,4a,9,9a-hexahydro-1 H-β-carboline.

17. The method of claim 14, wherein X has the formula $$NR^1-(CR^1{}_2)_n NR^3R^4 \qquad (5)$$

wherein $R^1$ is H; n is 1-6; and $R^3$ and $R^4$ together with N in $NR^3R^4$ form an optionally substituted ring.

18. The method of claim 17, wherein n is 2 or 3.

19. The method of claim 1, wherein each optionally substituted moiety in any compound having formula 2 or formula 4 may be substituted with one or more halo, $OR^2$, $NR^1R^2$, carbamate, $C_{1-10}$ alkyl, $C_{2-10}$ alkenyl, each optionally substituted by halo, C=O, aryl or one or more heteroatoms; aryl, carbocyclic or a heterocyclic ring.

20. The method of claim 1, wherein said compound having formula 2 is

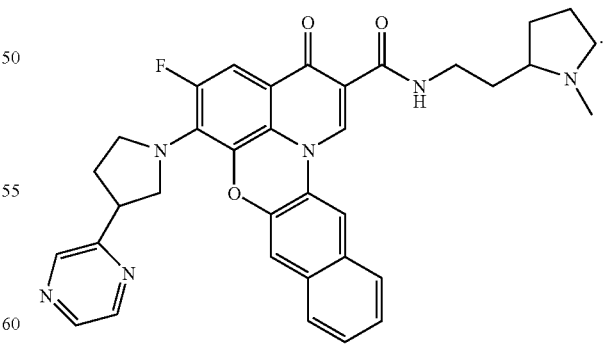

21. The method of claim 1, wherein said Lewis acid is $BL_3$, $AlL_3$, $FeL_3$, $GaL_3$, $SbL_5$, $InL_3$, $ZrL_4$, $SnL_4$, $TiL_4$, $TiL_3$, $AsL_3$, or $SbL_3$, wherein L is halo or alkyl.

22. The method of claim 21, wherein said Lewis acid is aluminum chloride.

23. The method of claim 1, wherein in —NR¹R², R² is $C_{1-10}$ alkyl or $C_{2-10}$ alkenyl substituted with a carbocyclic or heterocyclic ring.

24. The method of claim 23, wherein in —NR¹R², R² is $C_{1-10}$ alkyl substituted with a heterocyclic ring, where said heterocyclic ring is selected from tetrahydrofuran, 1,3-dioxolane, 2,3-dihydrofuran, pyran, tetrahydropyran, benzofuran, isobenzofuran, 1,3-dihydro-isobenzofuran, isoxazole, 4,5-dihydroisoxazole, piperidine, pyffolidine, pyrrolidin-2-one, pyrrole, pyridine, pyrimidine, octahydro-pyrrolo[3,4-b]pyridine, piperazine, pyrazine, morpholine, thiomorpholine, imidazole, imidazolidine-2,4-dione, 1,3-dihydrobenzimidazol-2-one, indole, thiazole, benzothiazole, thiadiazole, thiophene, tetrahydro-thiophene 1,1-dioxide, diazepine, triazole, guanidine, diazabicyclo[2.2.1]heptane, 2,5-diazabicyclo[2.2.1]heptane, 2,3,4,4a,9,9a-hexahydro-1H-β-carboline, oxirane, oxetane, tetrahydropyran, dioxane, lactones, aziridine, azetidine, piperidine, and lactams.

25. The method of claim 1, wherein the amine of formula NHR¹R² is 2-(2-aminoethyl)-1-methyl pyffolidine or 1-(2-aminoethyl) pyrrolidine.

26. The method of claim 1, wherein the amine of formula NHR¹R² is 2-(2-aminoethyl)-1-methyl pyffolidine.

27. The method of claim 1, wherein in —NR¹R², R² is an optionally substituted carbocyclic ring, heterocyclic ring, aryl or heteroaryl.

28. The method of claim 1, wherein NHR¹R² is an amine of the formula:

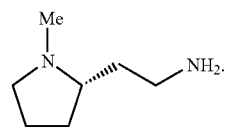

29. The method of claim 28, which produces a compound of formula (2), wherein said compound of formula (2) is:

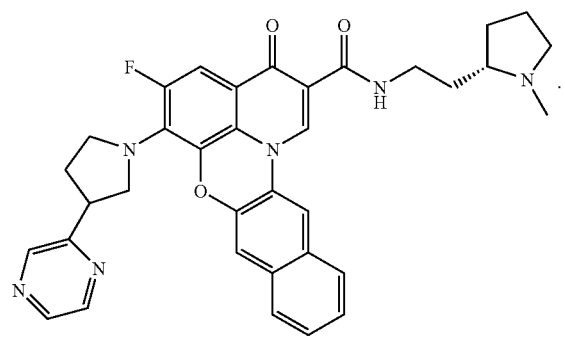

* * * * *

UNITED STATES PATENT AND TRADEMARK OFFICE
CERTIFICATE OF CORRECTION

PATENT NO. : 7,652,134 B2
APPLICATION NO. : 11/149007
DATED : January 26, 2010
INVENTOR(S) : Whitten et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 715 days.

Signed and Sealed this

Twenty-third Day of November, 2010

David J. Kappos
*Director of the United States Patent and Trademark Office*